United States Patent [19]
Gordon et al.

[11] Patent Number: 5,320,621
[45] Date of Patent: Jun. 14, 1994

[54] TECHNIQUE FOR INCORPORATING AN ELECTRODE WITHIN A NOZZLE

[75] Inventors: Mark G. Gordon, Corona del Mar; Charles E. Beuchat, Irvine, both of Calif.

[73] Assignee: Birtcher Medial Systems, Inc., Irvine, Calif.

[21] Appl. No.: 58,021

[22] Filed: May 5, 1993

[51] Int. Cl.$^5$ ............................................. A61N 1/04
[52] U.S. Cl. ...................................... 606/49; 128/639; 604/269; 606/129
[58] Field of Search ................... 604/269; 606/129, 32, 606/40, 151, 45, 49; 128/639, 642; 219/121.5, 121.51, 121.52

[56] References Cited
U.S. PATENT DOCUMENTS

| | | | |
|---|---|---|---|
| 2,808,833 | 10/1957 | August | 606/49 |
| 4,901,719 | 2/1990 | Trenconsky et al. | 606/49 |
| 5,098,430 | 3/1992 | Fleenor | 606/42 |

*Primary Examiner*—William E. Kamm
*Assistant Examiner*—Brian M. Green
*Attorney, Agent, or Firm*—John R. Ley; John B. Phillips

[57] ABSTRACT

A clip supports an elongated electrode within a nozzle of an electrosurgical handpiece used in gas electrocoagulation. The clip is preferably formed from a cylindrical tube which has been deformed into a configuration which has a central conduit-like section which engages and supports the electrode and two opposed conduit-like lobe portions which extend outward and slightly compress against the nozzle to hold the electrode and clip in place in the nozzle. The clip is formed by deforming a segment of a cylindrical tube into the clip around the tube. The clip and the attached electrode are inserted into the nozzle by resiliently compressing the clip by inserting a narrow end of the clip into a rear end of the nozzle and pushing the clip and the nozzle together, thereby resiliently compressing the clip as it slips into the nozzle.

32 Claims, 3 Drawing Sheets

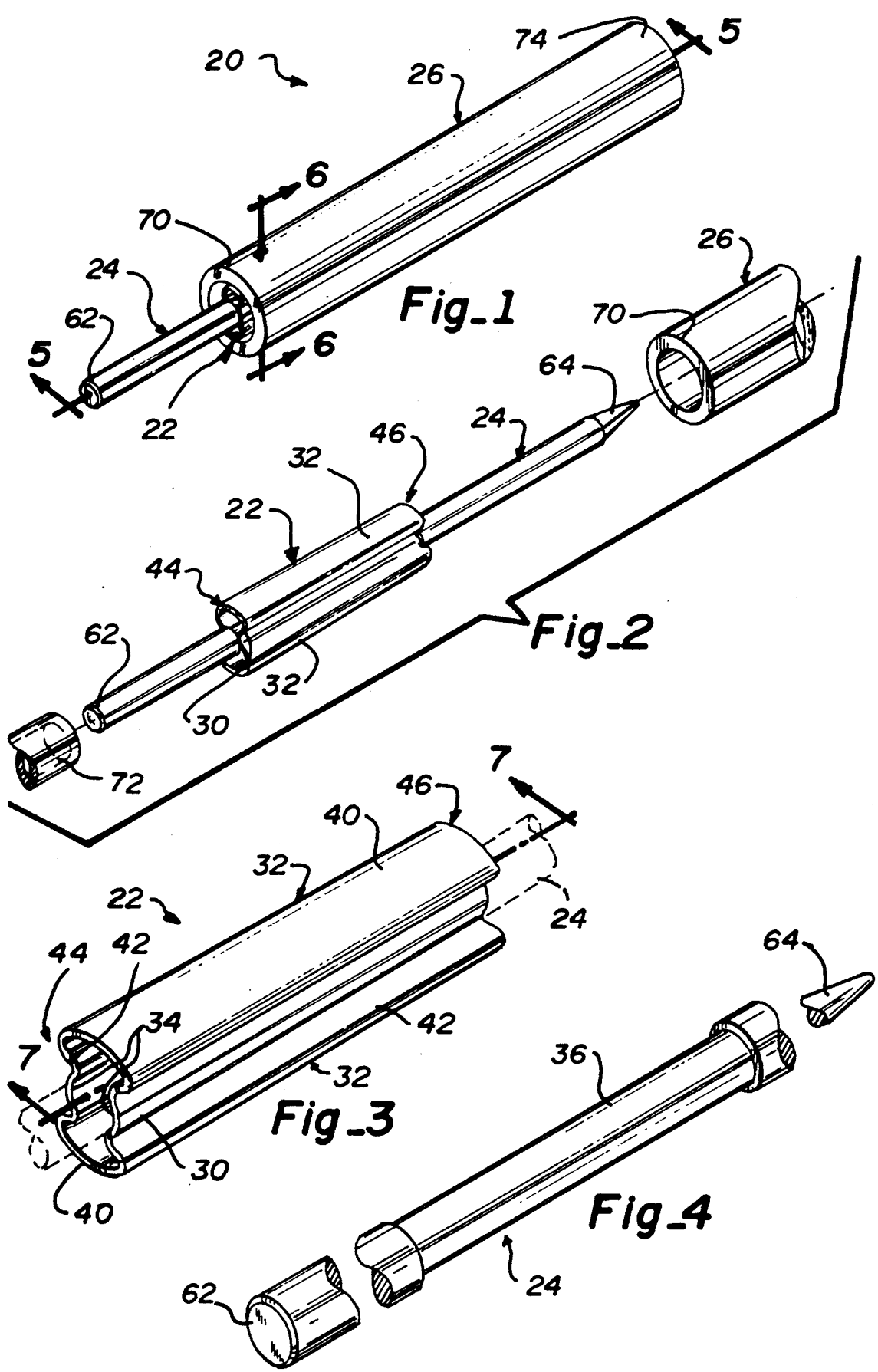

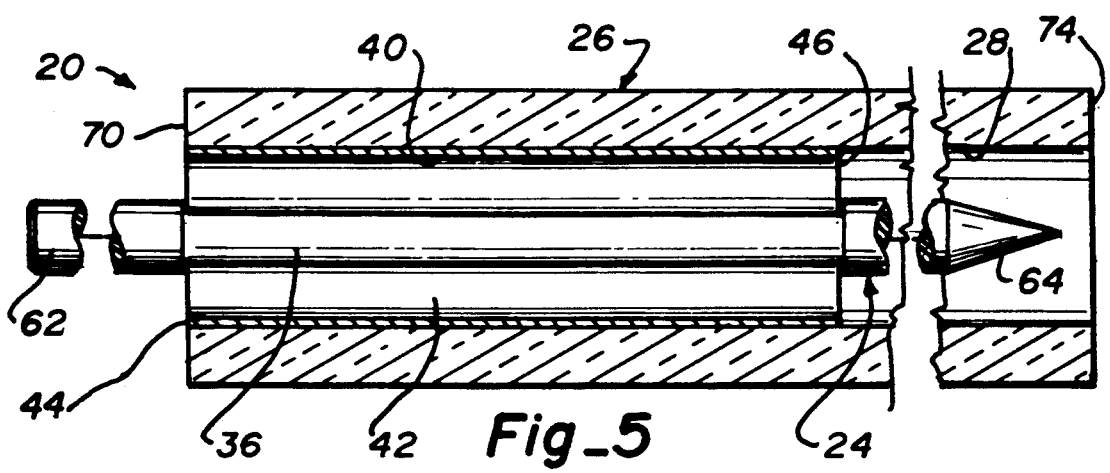
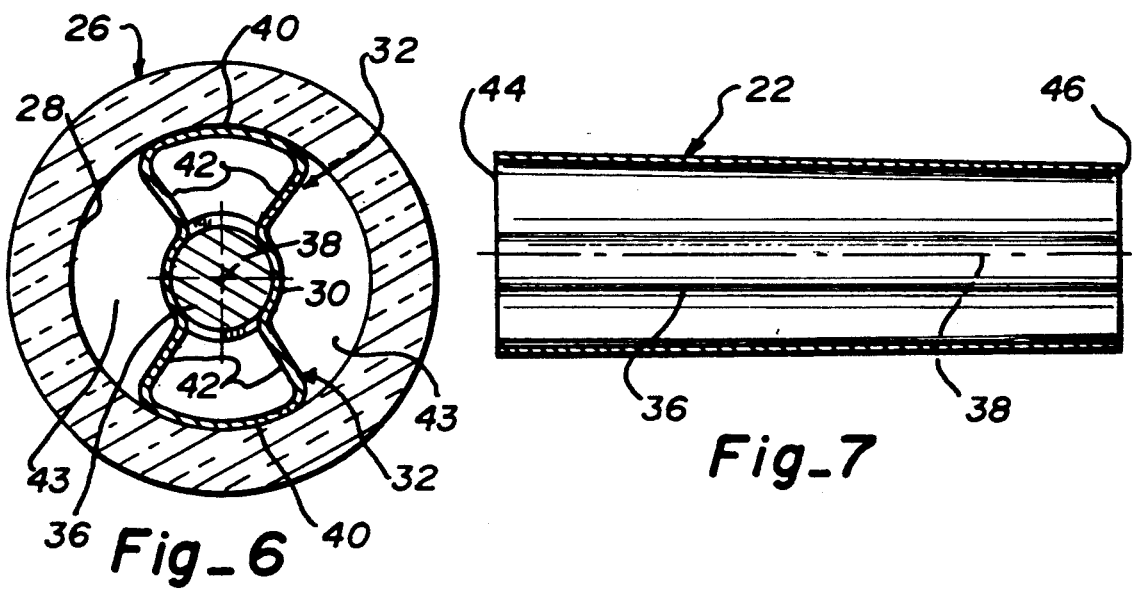
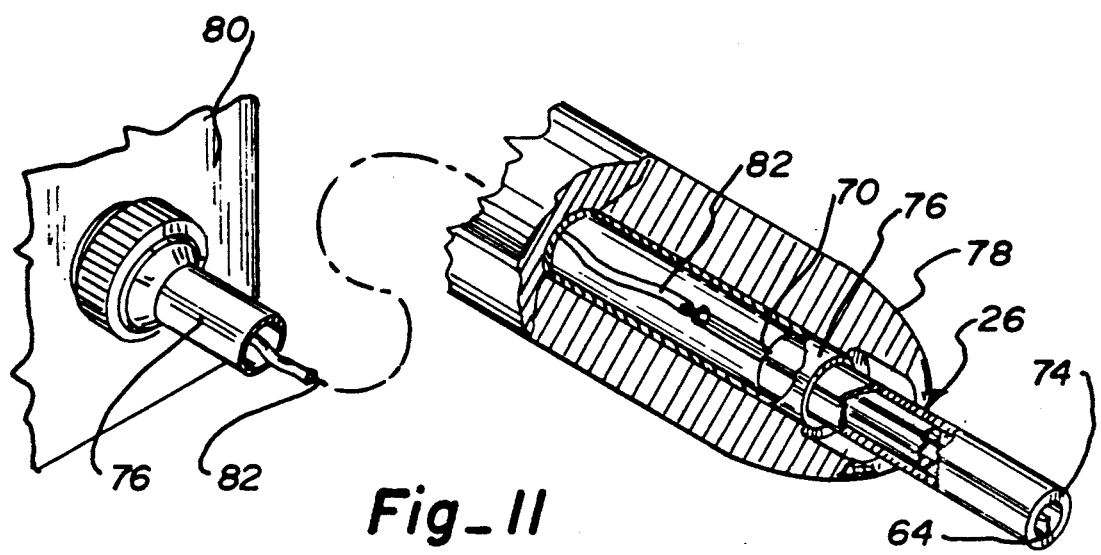

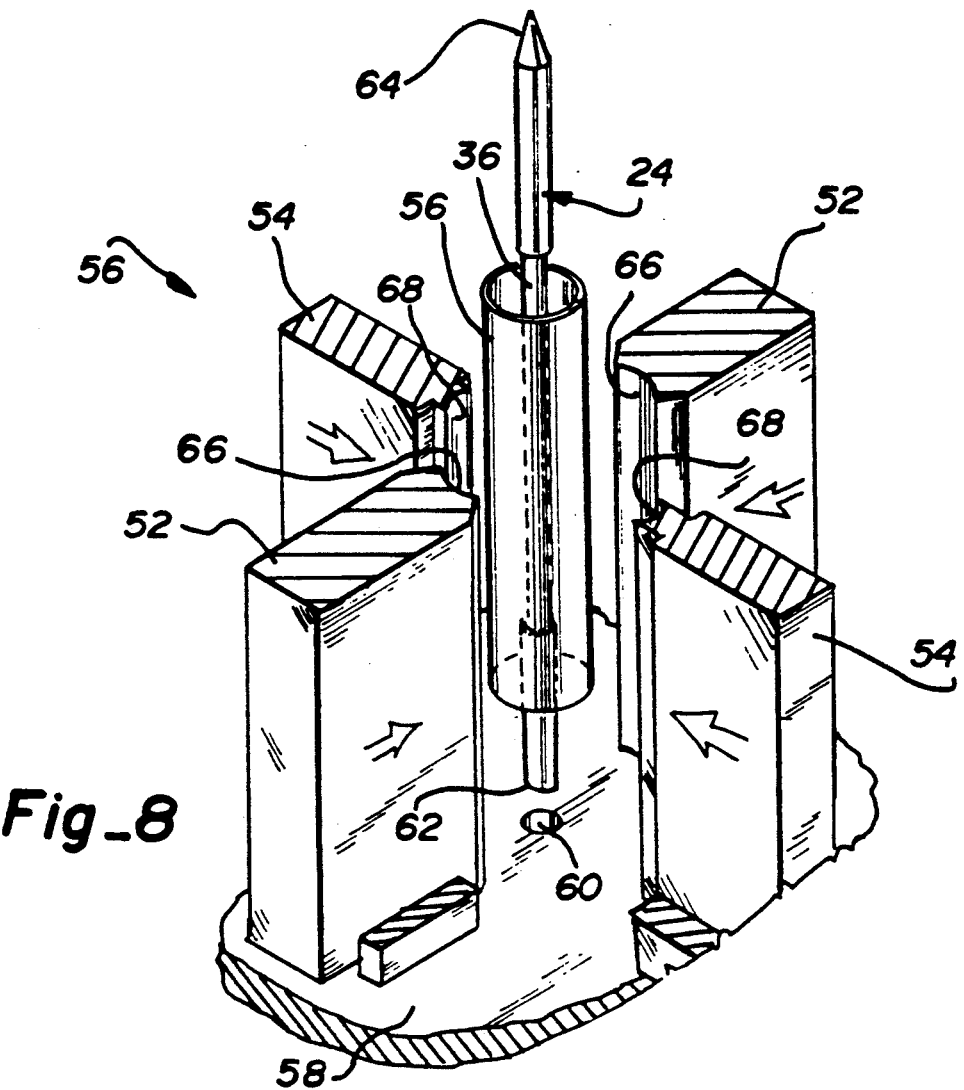
Fig_8
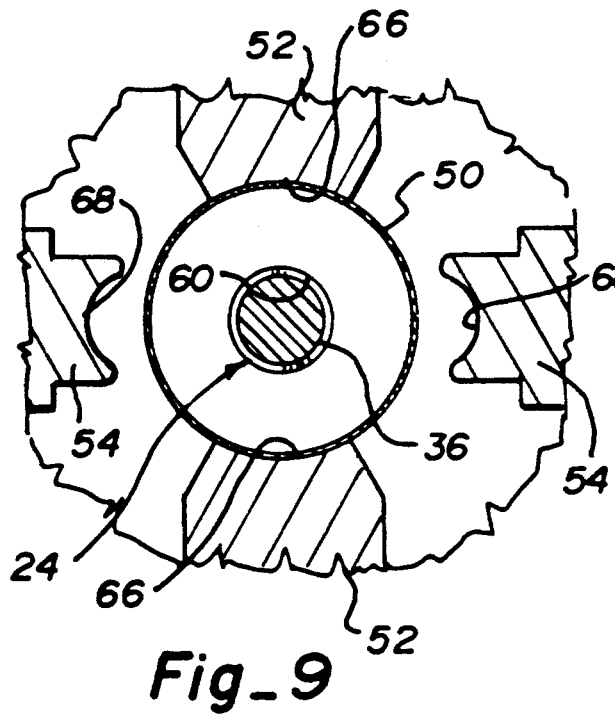
Fig_9
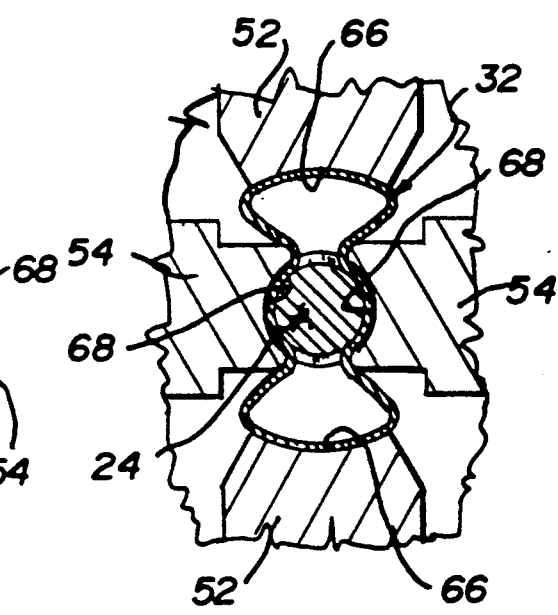
Fig_10

TECHNIQUE FOR INCORPORATING AN ELECTRODE WITHIN A NOZZLE

FIELD OF THE INVENTION

This invention pertains to electrosurgery, and more particularly, to a new and improved technique for incorporating an electrode within a nozzle of an electrosurgical handpiece utilized during conductive gas electrocoagulation.

BACKGROUND OF THE INVENTION

Electrocoagulation involves the coagulation of bleeding tissue by the application of electrical energy to the tissue. Conductive gas electrocoagulation involves conducting electrical energy to the tissue as arcs in ionized conductive pathways in a flowing stream of inert gas. A more complete description of conductive gas electrocoagulation is available in U.S. Pat. Nos. 4,781,175, 4,901,719, and 4,901,720, all assigned to the assignee of the present invention.

During conductive gas electrocoagulation, the conductive gas jet is typically delivered to the tissue by a handpiece that the surgeon manipulates. Gas and electrical energy are delivered from an electrosurgical apparatus to a transfer electrode located within an electrically insulated gas nozzle located within the handpiece. The gas flows through the nozzle and over the electrode where it is ionized by the electrical energy applied to the electrode. Electrical energy is transferred from the electrode as arcs in conductive pathways in the gas flowing to the tissue.

It is desirable that the transfer electrode be fixedly mounted and centered within the gas nozzle, to achieve the best energy transfer and electrical insulating characteristics. Furthermore, the energy transfer characteristics are enhanced by exposing a maximum amount of the electrode to the flow of gas within the nozzle. As a result of these and other considerations, prior art handpieces have utilized complex structures to center the electrode within the nozzle.

Prior art handpieces, as typified by U.S. Pat. Nos. 4,781,175 and 4,901,719, have required the construction of a one piece ceramic molded nozzle and electrode assembly to retain and center the electrode within the nozzle. The molded assembly is formed by centering the electrode within a mold, inserting ceramic material into the mold, and allowing the ceramic material to harden around the electrode. Once completed, the nozzle and electrode assembly is secured to the remainder of the electrosurgical handpiece. Although effective, these prior art nozzle and electrode assemblies are somewhat costly to manufacture, due to the costs of the insert molding used to form the assembly.

The nozzle and electrode assembly described in U.S. patent application Ser. No. 592,810, also assigned to the assignee of the present invention, is a unitary, molded assembly which is slip fit within a gas supply tubing at the handpiece. This type of assembly reduces the cost of a conductive gas electrocoagulation handpiece because of its convenient use of the gas supply tubing to achieve some of the functionality of the handpiece. However, the structure which creates the nozzle and supports the electrode is still a single molded unit.

Alternatives to molding the nozzle and electrode supporting structure around the electrode involve the use of centering devices to locate the electrode within a length of prefabricated ceramic tubing which serves as the nozzle. This type of support is generally located at a midpoint of the electrode and is intended to function in conjunction with another support at the rear of the electrode to maintain the electrode in the center of the nozzle. U.S. Pat. No. 4,040,426 is an example of such an arrangement. As described in this patent, the support member supports the electrode only along a limited length of the electrode, and thus the rear end of the electrode requires additional support within the handpiece body. One difficulty with this type of arrangement is maintaining the electrode in the centered position. Movement of either the middle or rear support can shift the position of the electrode and adversely affect its operating characteristics. Furthermore, although this support arrangement is simple in concept, it can be difficult to employ practically because of difficulty in assembling the nozzle, electrode and handpiece to obtain support for the rear end of the electrode.

It is with regard to this background information that the improvements available from the present invention have evolved.

SUMMARY OF THE INVENTION

One of the significant aspects of the present invention relates to a clip for supporting an elongated electrode within a nozzle which directs a flow of gas from an electrosurgical handpiece. The clip comprises a central section having opposed and facing surfaces to frictionally engage and extend longitudinally along an electrode and to support the electrode in a predetermined manner in the nozzle. The clip also includes a plurality of legs connected to the central section and extending transversely outward from the central section to contract the nozzle and to position the center section within the nozzle at a location spaced from the nozzle. Preferably the legs preferably form part of conduits which extend longitudinally along the nozzle. Each conduit is formed as a lobe which extends on opposite sides of the center section and the lobes contact the nozzle. The conduits are resilient and resiliently compress against the nozzle to hold the clip in the nozzle. The longitudinal extent of contact of the central section with an electrode and the longitudinal extent of contact of the legs along the nozzle are sufficient to prevent substantial movement or angular deflection of the electrode away from the predetermined position. The conduit-like configurations are tapered in a forward converging manner toward a forward end of the electrode, and upon insertion into the nozzle the compression of the resilient material holds the clip in place.

In accordance with another of its aspects the present invention relates to a method of forming the clip. The method includes positioning a segment of a cylindrical tube in a press and molding device and deforming the tube into the clip. The electrode may be attached to the clip by positioning the electrode within the central partial conduit of the clip, or by inserting the electrode into the tube and deforming the tube into the clip around the electrode. In addition the clip and the attached electrode are inserted into a nozzle by resiliently compressing the clip by inserting the narrow end of the clip into a rear end of the nozzle and pushing the clip and the nozzle together after the narrow end is inserted to resiliently compress the wider portions of the clip as the clip slips into the nozzle. The clip is retained in the nozzle by the resilient compression against the nozzle.

By structuring and manufacturing the clip in the manner described, and by supporting the electrode with the clip and by retaining the electrode and the clip in the nozzle, substantial improvements in the cost and efficiency in manufacturing and in the effectiveness and integrity of the resulting clip and electrode and nozzle assemblies result.

A more complete appreciation of the present invention and its scope can be obtained from understanding the accompanying drawings, which are briefly summarized below, the following detailed description of a presently preferred embodiment of the invention, and the appended claims.

BRIEF DESCRIPTION OF THE DRAWINGS

FIG. 1 is a perspective view of a nozzle and electrode assembly embodying the present invention.

FIG. 2 is an exploded perspective view of the assembly illustrated in FIG. 1, showing an electrode clip, an electrode and a nozzle, and a tool for inserting the electrode and clip into the nozzle.

FIG. 3 is an enlarged perspective view of the electrode clip illustrated in FIG. 2, with a portion of the electrode shown in phantom.

FIG. 4 is an enlarged fragmentary perspective view of the electrode illustrated in FIG. 2, showing an undercut portion of the electrode contacted by the electrode clip.

FIG. 5 is an enlarged longitudinal section view of the nozzle and electrode assembly taken substantially in the plane of line 5—5 of FIG. 1, with a portion broken out.

FIG. 6 is an enlarged cross section view of the nozzle and electrode assembly taken substantially in the plane of line 6—6 in FIGS. 1 and 5.

FIG. 7 is an enlarged section view taken substantially in the plane of line 7—7 of FIG. 3, showing a taper in one dimension of the electrode clip.

FIG. 8 is a generalized perspective view of a press mold and assembly device used in the formation of the electrode clip illustrated in FIG. 2, with a portion broken out to illustrate details of the mold.

FIG. 9 is a generalized horizontal sectional view of the device shown in FIG. 8, with a blank tube shown within the device.

FIG. 10 is a horizontal sectional view of the device shown in FIG. 9, showing deformation of the blank tube about the electrode to form the electrode clip illustrated in FIG. 2.

FIG. 11 is a perspective view of the nozzle and electrode assembly illustrated in FIG. 1, in conjunction with an electrosurgical handpiece and an electrosurgical apparatus.

DETAILED DESCRIPTION

A nozzle and electrode assembly 20 which incorporates the present invention is shown in FIG. 1. One aspect of the present invention relates to an electrode clip 22 which is shown in FIGS. 2 and 3. The clip 22 retains and centers an electrode 24 within a cylindrical nozzle 26 of the assembly 20. The clip 22 grips the electrode 24 and is positioned within the nozzle 26 to center the electrode 24 along the longitudinal axis of the nozzle 26. The clip 22 supports the electrode 24 in such a manner and along a sufficient amount of the length of the electrode so as to maintain the electrode in a coaxial position within the nozzle 26 with no additional support.

The nozzle 26 is preferably a conventional tubular structure made from a non-conductive ceramic material. The nozzle 26 has an inner cylindrical surface 28 of a predetermined uniform diameter.

The electrode clip 22 is preferably a hollow tubular structure having a cross-sectional shape shown in FIGS. 3 and 6. The cross-sectional shape includes a rounded central section 30 with two adjacent lobes 32 on opposite sides of the central section 30. The central section 30 includes two opposed and facing arcuate surfaces 34 which contact and grip a cylindrical segment 36 of the electrode 24. The cross-sectional shape of the clip 22 is generally symmetrical about a longitudinal axis 38 as shown in FIG. 6. The cross-sectional shape is also such that one-half is a mirror image of the other half, with respect to both a horizontal and a vertical plane extending through the axis 38. The central section 30 is centered about the axis 38, and the two lobes 32 are positioned radially opposite one another with respect to the axis. An outer cylindrical surface of an outer curved portion 40 of each lobe 32 contacts the inner cylindrical surface 28 of the nozzle 26. Leg portions 42 extend between the outer curved portion 40 of the lobes 32 and the arcuate surfaces 34 of the central section 30. Arranged in this manner, the clip has a cross-sectional configuration somewhat similar to the shape of a figure eight, a hour glass, a bow-tie or a butterfly, as shown in FIG. 6.

The electrode 24 is typically constructed from tungsten, and the cylindrical segment 36 of the electrode is preferably undercut, as shown in FIG. 4, to provide a more secure gripping area for the arcuate surfaces 34 of the clip 22. The length of the clip 22 extends a substantial distance along the length of the electrode 24. This longitudinal distance is sufficient to hold the electrode coaxially in the nozzle without additional support for the electrode. The length of the clip 22 and its contact at the cylindrical segment 36 is sufficient to prevent the electrode from moving off of the longitudinal axis of the nozzle. As an example in the preferred embodiment, the length of the clip 22 is approximately 0.38 inches and the length of the nozzle 26 is approximately 0.90 inches.

The described cross-sectional configuration of the clip 22 creates three generally tubular portions or areas. A center tubular area is generally bounded by the opposing arcuate surfaces 34 of the central section 30. The center tubular area receives the undercut area formed by the cylindrical segment 36 of the electrode 24. The undercut area is cylindrical in cross-section as shown in FIG. 6. Each lobe 32 also creates a tubular portion formed generally by the legs 42 and the outer curved portion 40. The tube portions formed by the lobes 32 allow gas to pass therethrough and the gas thus maintains contact with the electrode 24 to further enhance the opportunities for gas ionization. In addition, open areas 43 on opposite sides of the clip allow gas to pass through the nozzle 26. Because the clip is preferably formed of electrically conductive metal which contacts the electrode, the presence of electrical potential and energy on the clip 22 also enhances the possibility of gas ionization. Thus, due to the structure of the clip 22, there is little impediment to the flow of gas through the nozzle 26 and the possibilities of ionization are enhanced because of the full exposure of the electrode 24 to the gas flowing in the nozzle.

The elevational height of the clip 22 tapers along the length of the clip, narrowing from a proximal or rear end 44 of the clip 22 to a distal or forward end 46 of the clip, as shown in FIG. 7. The magnitude of the taper is small, accounting for approximately a two percent variance between the heights of the proximal end 44 and the distal end 46 of the clip 22. The degree of taper shown in FIG. 7 has been exaggerated for illustrative purposes. The taper is such that the height of the clip at the distal end 46 is slightly less than the diameter of the inner cylindrical surface of the nozzle. The height of the clip at the proximal end 44 is greater than the diameter of the nozzle. Tapered in this manner, the distal end 46 of the clip is easily inserted within the nozzle 26 during assembly of the nozzle and electrode assembly 20. Forward movement during insertion results in slight radial compression of the resilient clip 22 to hold the clip and attached electrode 24 in place in the nozzle 26.

The clip 22 is preferably formed by pressing a predetermined length of blank cylindrical tube 50 between opposing retainers 52 and formers 54 in a press mold and assembly device 56, as shown in FIGS. 8-10. The device 56 includes a base plate 58 into which a vertical hole 60 is formed. The hole 60 is adapted to receive a proximal or rear end 62 of the electrode 24 and thereby supports the electrode to extend vertically upward from the base plate 58. A pointed forward or distal end 64 of the electrode 24 points upward when the electrode is retained in this manner.

The retainers 52 and the formers 54 are movably attached to the base plate 58 to move toward and away from the electrode 24 from four perpendicular directions. The retainers 52 and the formers 54 are attached to the base plate by conventional guide rails and connection arrangements (not specifically shown). Movement imparting or drive (also not shown), apparatus such as hydraulic or pneumatic cylinders or mechanical lever arrangements, move the retainers 52 and the formers 54 toward and away from the electrode 24.

The retainers 52 have partial cylindrical surfaces 66 which contact the outer surface of the tube 50. The radius of curvature of each of the surfaces 66 is approximately the same as the radius of curvature of the inner cylindrical surface 28 of the nozzle 26 (FIG. 6). The surfaces 66 longitudinally converge or taper toward one another and toward the electrode in a direction toward the front tip end 64 of the electrode 24. This converging taper is responsible for tapering the clip 22 in the manner shown in FIG. 7, when the tube 50 is transformed into the clip 22 by the device 56.

The formers 54 have die faces 68 which each have a partial cylindrical configuration generally similar to the exterior surface of the central section 30 of the clip 22 (FIG. 6). The die faces 68 contact the tube 50 and press or swage it around the undercut segment 36 of the electrode 24 (FIGS. 3-6) to form the central section 30 and to retain the clip 22 to the electrode 24.

To transform the tube 50 into the clip 22 attached to the electrode 24, the retainers 52 and the formers 54 are moved laterally inward toward the electrode 24. The retainers 52 first contact and hold the tube while deforming it to impart the longitudinal taper, and then the formers 54 move laterally inward to bend and deform the tube and complete the formation of the clip. The space between the formers and the retainers allows the tube 50 to bend into the cross-sectional shape shown as the formers press the tube into the central section 30. The figure eight, hour-glass, bow-tie or butterfly configuration assumed by the deformed tube occurs naturally without any holding or support other than that from the die faces 68 of the formers 54 and the surfaces 66 of the retainers 52.

A typical clip formation cycle begins with the retainers 52 and formers 54 of the device 56 in an open position as shown in FIG. 8. The electrode 24 is then positioned within the centering hole 60 so that the undercut cylindrical segment 36 is above the base plate 58. The electrode 24 is oriented so that the front tip end 64 extends out of the device 56. The cylindrical blank tube 50 is then inserted down and around the electrode 24, as shown in FIG. 9, until the tube sits on the base plate 58. The blank tube 50 is preferably made from stainless steel and is of a length equal to the length of the undercut cylindrical segment 36. In this position, the tube 50 is laterally aligned with the undercut segment 36.

Upon movement of the retainers 52 into contact with the tube 50, the tube is first tapered in the manner shown in FIG. 7. Thereafter, with movement of the formers 54, the tube 50 is then transformed into the clip 22 with the central sections 30 swaged around the undercut segment 36 of the electrode 24 as shown in FIG. 10.

The electrode 24 is neither deformed nor damaged as the clip 22 is molded around the electrode. Since the central section 30 of the clip 22 is formed about the undercut segment 36 of the electrode 24, the arcuate surfaces 34 of the central section 30 generally conform to the circumference of the undercut segment 36 to adequately retain the electrode 24. Contact between the ends of the central section 30 of the clip 22 and the larger diameter shoulders of the electrode adjacent to the undercut segment 36 will prevent longitudinal movement of the clip 22 along the electrode 24.

After forming the clip 22 around the electrode 24, the retainers 52 and the formers 54 are moved in the reverse direction to retract away from the clip. In this position the nozzle and electrode assembly 20 is then completed by inserting the nozzle 26 over the clip 22, while the clip and the attached electrode are in the device 56. With the retainers and the formers moved outward to a position separated from the clip 22, a rear end 70 of the ceramic nozzle 26 is positioned down on the front end 46 of the tapered clip 22. Because of its taper, the front end 46 of the clip 22 extends slightly into the rear end 70 of the nozzle. Once the tapered end forward end 46 has entered the rear end of the nozzle 26, the nozzle 26 is pushed downward over the remainder of the clip 22 until the rear end 70 of the nozzle is flush with the rear end 44 of the clip, both of which rest on the base plate 58. With the rear end 44 of the clip against the base plate 58, the clip is retained to allow the nozzle to be pressed down over it. Due to the resilient nature of the preferably metal clip 22, the lobes 32 are resiliently compressed as the clip 22 is press fit into the nozzle. The compression of the lobes 32 against the ceramic nozzle 26 during insertion of the clip holds the electrode and clip in place in the nozzle. The degree of compression is not sufficient to result in significant separation of the arcuate surfaces 34 from the undercut portion 36 of the electrode, so as to release or loosen the connection to the electrode.

An alternative to using the device 56 for assembling the clip and attached electrode into the nozzle is shown in FIG. 2. A cylindrical insertion sleeve 72 is utilized as a tool to push the clip 22 and attached electrode 24 into the nozzle 26 to the final retained position. The insertion sleeve 72 fits over the rear end 62 of the electrode 24 and presses against the rear end 44 of the clip 22 during this alternative assembly process. The assembled electrode 24 and clip 22 are inserted from the rear end of the nozzle so that the narrower forward end 46 of the clip 22 is the first portion of the clip to enter the nozzle. Once the tapered forward end 46 has entered the rear end 70 of the nozzle 26, the remainder of the clip 22 is pushed into the nozzle. By manipulating the insertion sleeve 72, the clip 22 is inserted within the nozzle 26 so that the rear end 44 of the clip is flush with the rear end 70 of the nozzle, as shown in FIG. 1.

The assembly of the clip and electrode into the nozzle allows the electrode 24 to be supported in a cantilever manner at its rear end so that the electrode is exposed to the gas within the nozzle 26. The lengths of the electrode 24 and nozzle 26, and the position of the undercut segment 36, are predetermined so that the front end tip 64 of the electrode 24 is positioned within the nozzle 26, preferably within 0.10 inches from extending from a front end 74 of the nozzle.

After assembly, the nozzle and electrode assembly 20 may be connected in a handpiece in a variety of different manners, including inserting the rear end 70 of the nozzle into the end of a gas supply tube 76, as shown in FIG. 11. The connection of the rear end 70 of the nozzle 26 to a gas supply tube 76 is preferably accomplished within an electrosurgical handpiece 78 as shown in FIG. 11. The gas supply tube 76 connects the handpiece 78 to an electrosurgical apparatus 80 which contains a supply of inert gas. Similarly, the rear end 62 of the electrode 24 is connected to any suitable electrical source, although it is preferably connected within the handpiece 78 to an electrical conductor 82 contained within the gas supply tube 76. The electrical conductor 82, in turn, is connected to an electrosurgical generator contained within the electrosurgical apparatus 80.

The electrical energy supplied by the electrosurgical generator in the apparatus 80 to the electrode 24 is of a predetermined character sufficient to ionize the inert gas flowing through the nozzle 26. In this manner, ionized conductive pathways are created in the gas jet flowing from the front end 74 of the nozzle 26. The electrical energy within the ionized pathways travels with the gas jet to a body tissue where it creates a predetermined electrosurgical effect on the tissue. The manner in which the nozzle and electrode assembly 20 is used in an electrosurgical handpiece will be apparent from the previously referenced U.S. patents and application of the assignee as well as others.

Significant improvements are available from the clip 22 and the nozzle and electrode assembly 20. Low cost prefabricated ceramic nozzles 26 may be used with the clips 22 in place of more costly injection molded parts where the nozzle is formed about the electrode. A substantial savings in the manufacturing costs of the nozzle and electrode assemblies results. The exposure of the electrode to the flow of gas through the nozzle is not restricted. The shape of the central section 30 and the lobes 32 of the clip 22 increase the surface area of the electrode 24 exposed to the gas within the nozzle 26, as shown in FIG. 6. In effect, the gas within the nozzle 26 flows through the tubular portions formed by the lobes 32 and contacts the electrode 24 not gripped by the arcuate surfaces 34 of the central section 30. Furthermore, forming the clip 22 from conductive stainless steel may enhance the electrical field effect generated by the electrode 24 to enhance gas ionization. Thus, the shape and the steel construction of the clip 22 combine to enhance the initiation of the electrical energy transfer. The clip and electrode are quickly and conveniently joined as a single assembly by the die press molding technique described. The electrode and clip are easily assembled into the nozzle, and are held in the desired position without the need for other supports. The assembly can be conveniently slip fit into the end of a gas supply tubing.

A presently preferred embodiment of the present invention and many of its improvements have been described with a degree of particularity. This description has been made by way of preferred example and is based on a present understanding of knowledge available regarding the invention. It should be understood, however, that the scope of the present invention is defined by following claims, and not necessarily by the detailed description of the preferred embodiment.

The invention which is claimed is:

1. A clip for supporting an elongated electrode within a nozzle which directs a flow of gas from an electrosurgical handpiece, comprising:
    a central section having opposed and facing surfaces adapted to frictionally engage and extend longitudinally along an electrode and support the electrode in a predetermined position within the nozzle; and
    a plurality of legs connected to the central section and extending transversely outward from the central section, said legs adapted to contact the nozzle and position the central section within the nozzle at a location spaced from the nozzle.

2. A clip as defined in claim 1 wherein:
the legs define vanes adapted to direct the gas within the nozzle.

3. A clip as defined in claim 1 wherein:
the legs form part of at least one conduit adapted to extend longitudinally along the nozzle.

4. A clip as defined in claim 3 wherein:
each conduit is resilient and each conduit is adapted to be resiliently compressed against the nozzle to hold the clip in the nozzle.

5. A clip as defined in claim 1 wherein:
the legs are adapted to longitudinally contact the nozzle; and
the longitudinal extent of contact of the central section with the electrode and the longitudinal extend of contact of the legs along the nozzle are sufficient to prevent substantial angular deflection of the electrode away from the predetermined position.

6. A clip as defined in claim 1 wherein:
the legs extend from the center section to an outer curved portion; and
the outer curved portion is adapted to contact the nozzle.

7. A clip as defined in claim 6 wherein:
two leg portions join a single outer curved portion; and
the two leg portions and the single outer curved portion form a conduit-like configuration.

8. A clip as defined in claim 7 further comprising a plurality of conduit-like configurations adapted to extend longitudinally along the nozzle.

9. A clip as defined in claim 8 wherein:
each conduit-like configuration is tapered in a forward converging manner toward a forward end of the clip; and
the extent of the taper allows the plurality of conduit-like configurations to be inserted at the forward end of the clip into the nozzle.

10. A clip as defined in claim 9 wherein:
material; and
a maximum dimension between two opposing outer curved portions at a rear end of the clip is greater than a maximum cross-sectional dimension of the nozzle.

11. A clip as defined in claim 10 wherein:
the conduit-like configurations are adapted to apply frictional force against the nozzle to retain said clip in position in the nozzle.

12. A clip as defined in claim 1 formed from a tube and having a predetermined cross-sectional configuration defining three laterally adjacent generally curved sections, one of the curved sections including the central section, the two other curved sections including two lobes extending on opposite sides of the central section and adapted to contact opposing points on the nozzle, the lobes having a hollow cross-section to allow gas to pass through the lobes along the length of the tube.

13. A clip for use in supporting an elongated electrode within a cylindrical nozzle which directs a flow of gas from an electrosurgical handpiece, comprising:
three laterally adjacent partially closed conduits having coplanar centerlines, the conduits adapted to extend from one point on a circumference of the cylindrical nozzle to a diametrically opposed point on the circumference of the cylindrical nozzle, wherein the three partially closed conduits include:
a central partial conduit having opposed and facing arcuate surfaces adapted to engage the electrode; and
two lobe-shaped partial conduits extending from opposite sides of the central partial conduit and adapted to contact the diametrically opposed points on the circumference of the cylindrical nozzle, the lobe-shaped partial conduits adapted to allow gas within the nozzle to pass both around and through the lobe-shaped partial conduits.

14. A clip as defined in claim 13 wherein the lobe-shaped partial conduits are formed from a resilient material which allows the lobe-shaped partial conduits to compress and apply frictional force radially against the circumference of the nozzle.

15. A clip as defined in claim 13 wherein a maximum cross-sectional dimension of the clip is tapered along the length of the clip.

16. A clip as defined in claim 13 wherein the central partial conduit is adapted to engage a cylindrical segment of the electrode having a reduced diameter relative to adjacent cylindrical segments of the electrode.

17. A nozzle and electrode assembly to be used in conjunction with a handpiece for supplying electrical energy and gas from an electrosurgical apparatus to perform conductive gas electrocoagulation, comprising:
an elongated cylindrical nozzle adapted to apply the gas to a patient;
a clip which is separate from the nozzle and which is inserted into and frictionally retained within a rear end of the nozzle, the clip including a central partial conduit having opposed and facing arcuate surfaces and two lobe-shaped partial conduits extending from opposite sides of the central partial conduit to contact an interior circumference of the cylindrical nozzle at diametrically opposing points; and
an elongated electrode retained between the arcuate surfaces of the central partial conduit, the electrode extending within the nozzle along a longitudinal axis of the cylindrical nozzle.

18. A nozzle and electrode assembly as defined in claim 17, wherein the clip is formed from a resilient material, each lobe-shaped partial conduit includes an outer curved portion which conforms substantially to the interior circumference of the cylindrical nozzle, and the electrode is frictionally retained within the central partial conduit from resilient engagement with the arcuate surfaces.

19. A nozzle and electrode assembly as defined in claim 17, wherein the clip is formed from a resilient material, and a dimension of the clip between the diametrically opposing points is reduced along the length of the clip from a rear end thereof to a front end thereof, prior to insertion of the clip in the nozzle.

20. A nozzle and electrode assembly as defined in claim 19, wherein the length of the clip is less than one half of the length of the elongated electrode.

21. A nozzle and electrode assembly as defined in claim 17, wherein the portion of the electrode retained within the central partial conduit has a reduced diameter relative to adjacent portions of the electrode.

22. A method of forming a clip used to retain and center an elongated electrode within a cylindrical nozzle in a handpiece of a conductive gas electrocoagulation device, said method comprising the steps of:
positioning a segment of a cylindrical tube in a die pressmold device; and
deforming the tube into said clip by forming a central partial conduit and two lobe-shaped partial conduits attached to opposite sides of the central partial conduit.

23. A method of forming the clip as defined in claim 22 further comprising the step of:
reducing the greatest cross-sectional dimension of the clip from one end along the length of the clip to the other end of the clip.

24. A method of forming an electrode and clip assembly used to retain and center an elongated electrode within a cylindrical nozzle, said method comprising the step of:
positioning a segment of a cylindrical tube in a die pressmold device;
deforming the tube into a clip by forming a central partial conduit and two lobe-shaped partial conduits attached to opposite sides of the central partial conduit; and
attaching an elongated electrode within the central partial conduit of the clip.

25. A method as defined in claim 24, wherein attaching the electrode within the central partial conduit further comprises the steps of:
positioning the electrode into the tube along a longitudinal axis of the tube; and
deforming the tube into the clip around the electrode.

26. A method as defined in claim 25 further comprising the step of:
contacting the electrode substantially only by the central partial conduit after deforming the tube into the clip around the electrode.

27. A method of forming an assembly of a cylindrical nozzle and an elongated electrode and a clip to retain and center the elongated electrode within the cylindrical nozzle, said method comprising the steps of:

positioning a segment of a cylindrical tube in a die pressmold device;

deforming the tube into a clip by forming a central partial conduit and two lobe-shaped partial conduits attached to opposite sides of the central partial conduit;

attaching the electrode within the central partial conduit of the clip;

inserting the clip and the attached electrode into the nozzle; and centering the electrode within the nozzle by positioning the clip within the nozzle.

28. A method as defined in claim 27 further comprising the step of:

retaining the clip and electrode in the nozzle by friction resulting from resiliently compressing the clip due to insertion in the nozzle.

29. A method as defined in claim 28 further comprising the steps of:

narrowing the greatest cross-sectional dimension of the clip from one end along the length of the clip to the other end of the clip prior to inserting the clip in the nozzle;

inserting the narrow end of the clip into a rear end of the nozzle; and pushing the clip and the nozzle together after the narrow end is inserted in the nozzle to insert the clip in the nozzle and to resiliently compress the clip.

30. A method as defined in claim 29 further comprising the step of:

inserting the clip into the nozzle until a rear end of the clip is adjacent to the rear end of the nozzle.

31. A method as defined in claim 29 further comprising the step of:

inserting the clip into the nozzle until a front end of the electrode is adjacent to a front end of the nozzle.

32. A method as defined in claim 27 for use with a handpiece to perform conductive gas electrocoagulation, further comprising the steps of:

attaching the nozzle and electrode and clip assembly to the handpiece;

connecting the handpiece to an electrosurgical apparatus;

delivering gas and electrical energy to the nozzle and the electrode, respectively; and performing conductive gas electrocoagulation using the handpiece and the electrosurgical apparatus.

* * * * *